(12) United States Patent
Olsson et al.

(10) Patent No.: US 7,993,318 B2
(45) Date of Patent: Aug. 9, 2011

(54) ABSORBENT ARTICLE FOR MEN

(75) Inventors: Ken Olsson, Vastra Frolunda (SE); Hans Hedstrom, Molnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 578 days.

(21) Appl. No.: 11/576,318

(22) PCT Filed: Dec. 6, 2004

(86) PCT No.: PCT/SE2004/001802
§ 371 (c)(1),
(2), (4) Date: Mar. 29, 2007

(87) PCT Pub. No.: WO2006/062444
PCT Pub. Date: Jun. 15, 2006

(65) Prior Publication Data
US 2009/0182297 A1    Jul. 16, 2009

(51) Int. Cl.
*A61F 13/15* (2006.01)
(52) U.S. Cl. .............. 604/385.13; 604/358; 604/385.09; 604/385.19
(58) Field of Classification Search ............. 604/385.13, 604/385.09, 385.19, 358
See application file for complete search history.

(56) References Cited

U.S. PATENT DOCUMENTS

| 4,257,418 | A | * | 3/1981 | Hessner | 604/397 |
| 5,558,659 | A | * | 9/1996 | Sherrod et al. | 604/385.26 |
| 5,810,799 | A | | 9/1998 | Slater | |
| 6,402,729 | B1 | | 6/2002 | Boberg et al. | |

FOREIGN PATENT DOCUMENTS

| GB | 2284552 | 6/1995 |
| WO | 91/07155 A1 | 5/1991 |
| WO | 2004/004617 | 1/2004 |

* cited by examiner

*Primary Examiner* — Melanie J Hand
*Assistant Examiner* — Ginger T Chapman
(74) *Attorney, Agent, or Firm* — Buchanan Ingersoll & Rooney PC

(57) ABSTRACT

Absorbent article for men intended for single use and having longitudinal side edges, a rear end edge and a front end edge and having an inner liquid-permeable surface layer, an outer liquid-impermeable surface layer and an absorbent body arranged therebetween. The article has an elastic element attached to the liquid-permeable surface layer along at least parts of the longitudinal side edges of the article. The elastic element is attached to the liquid-permeable surface layer along longitudinal edges lying opposite one another of the elastic element. A cut is arranged between the attachments in the form of a slit or cutout. The cut extends through a front edge of the elastic element in the direction of a rear edge, the elastic element being provided by the cut with inner edges arranged above the liquid-permeable surface layer, and a method for manufacturing such an article.

16 Claims, 3 Drawing Sheets

ABSORBENT ARTICLE FOR MEN

TECHNICAL FIELD

The present invention relates to an absorbent article for men, intended for single use, and a method for manufacturing such an article.

BACKGROUND ART

In practice, it is possible to use conventional diapers as incontinence protection for men. The disadvantage of conventional diapers is that they are intended to absorb both urine and faecal matter and that they are therefore not suitable for men who only need protection which collects urine. Conventional diapers are relatively unwieldy with thick, wide absorbent bodies which during use extend the whole way from the abdomen area of the wearer, through the crotch and a considerable way up over the behind of the wearer. For reasons of both comfort and discreetness, there is a great need for more appropriate products for incontinent men.

Mild incontinence is a major and concealed handicap from which many men suffer and which seriously limits their possibilities for a normal active life. A large group which suffers from this is men with prostate problems. After operations, these men are usually affected by dribbling incontinence, which causes great distress.

Incontinence pads for men with mild incontinence are previously known per se but they have not functioned satisfactorily in all respects. Examples of previously known incontinence pads for men are those of the kind which have a container-like part for surrounding the genitals of the male wearer. Major disadvantages of these are that they are much too warm at the same time as they are too tight and consequently uncomfortable for the wearer.

Another disadvantage of this type of protection is that they are too stiff and can give rise to chafing.

One example of a previously known incontinence pad for men is described in WO 91/07155. This pad has an absorbent body which tapers towards one end from a front portion of the article to a crotch portion of the article and is enclosed in a covering consisting of a liquid-impermeable layer on one side of the absorbent body and a liquid-permeable layer on the opposite side of the absorbent body. The two layers extend outside the absorbent body and are interconnected there. The incontinence pad in this publication is provided with elastic threads or the like, which are applied with pretensioning to the covering on both sides of the absorbent body and which converge in the direction of the narrower end portion of the absorbent body.

The elastic threads and the tapering absorbent body interact to provide the pad with a bowl-like part at the bottom, which bowl-like part is intended during use of the pad to curve in under the penis and scrotum of the wearer.

A disadvantage of the construction according to WO 91/07155 is that undesirable folds extending from the absorbent body in the lateral direction can lead to urine leakage along the folds and out of the article.

Another incontinence pad for men is described in WO 2004/004617. This incontinence pad also has an absorbent body tapering from the front portion to the rear portion. A liquid barrier is arranged at the narrower end of the incontinence pad. This liquid barrier can be formed by a material piece which has been folded or bent into a suitable shape in order to follow the shape of the absorbent body at the narrow end. The liquid barrier can be provided with an elastic element applied along the edge of the barrier, a barrier raised above the liquid-permeable layer being formed.

The disadvantages of a barrier arranged according to WO 2004/004617 are that the process for applying the barrier can be complicated as the material piece forming the liquid barrier is bent or folded before application.

SUMMARY

An article of the kind referred to in the introduction which essentially eliminates the problems of previously known such articles has been produced. The article is characterized mainly in that the elastic element comprises an elastic material piece and is attached to the liquid-permeable surface layer along longitudinal outer edges of the elastic element, and in that a cut in the form of a slit or cutout is arranged in the longitudinal direction between the attachments, which cut extends through a front edge of the elastic element in the direction of a rear edge to an end point of the cut, the elastic element being provided by means of the cut with longitudinal inner edges arranged above the liquid-receiving surface layer so that a pocket is formed between the elastic element and the liquid-permeable surface layer.

The elastic element is therefore formed by elastic layer material which has been cut and also stretched and shaped so that it essentially follows the edge contour of the incontinence pad. In this connection, the elastic element is preferably formed by rectangular pieces of an elastic material web. However, it is alternatively possible to form the elastic element from elastic material pieces of a different shape, such as trapezoidal or triangular.

The elastic element is arranged at least in the rear portion of the article, the article having in the rear portion a shape curved in towards the wearer, the rear portion being intended during use to curve in under the penis and scrotum of the wearer.

The elastic element is preferably attached to the liquid-permeable surface layer in a stretched state, but it is also possible within the scope of the invention to apply elastic material which can be activated after application, for example elastic material comprising at least one layer which contracts when warmed. It is previously known to apply such materials in absorbent articles.

According to one embodiment, the distance between the inner edges obtained by means of the cut and the attachment of the elastic element along its longitudinal outer edges is at least 5 mm, preferably at least 10 mm or most preferably at least 15 mm. The distance between the attachment along the outer edges of the elastic element and the inner edges obtained by means of the cut should not be greater than 40 mm, preferably at most 30 mm or more preferably at most 25 mm. When determining the distance between the attachment and the inner edge, the shortest distance between a point on the inner edge and a point where the elastic element is attached to the liquid-permeable surface layer is measured.

The elastic element is suitably attached to the liquid-permeable surface layer along the rear edge of the elastic element as well. The distance between the end point of the cut and the attachment of the elastic element along the rear edge is suitably at most 50 mm, preferably at most 40 mm and more preferably at most 30 mm.

The elastic material is elastic at least in the longitudinal direction of the article.

According to one embodiment, the material included in the elastic element comprises elastic non-woven or a laminate of non-woven and an elastic plastic film.

According to one embodiment, the elastic material is hydrophobic.

A method of manufacturing absorbent articles comprises the following steps, preferably in the order indicated:

providing a first material web running in a transport direction and comprising absorbent bodies arranged between a lower, preferably liquid-impermeable surface layer and an upper, preferably liquid-permeable surface layer, providing a second material web comprising elastic material and running in a transport direction, cutting the second material web into individual elastic pieces, cutting the material between outer longitudinal edges in its elastic direction through a transverse edge in the direction of an opposite transverse edge to an end point so that a cut in the form of a slit or cutout is formed between longitudinal inner edges, applying the elastic pieces to the liquid-permeable surface layer on the first material web, attaching the elastic pieces to the liquid-permeable surface layer along the outer longitudinal edges of the elastic pieces, cutting the first material web, individual articles being formed.

According to one embodiment, the elastic material is stretched, and the application to the liquid-permeable surface layer is carried out with the elastic material in an extended state.

According to one embodiment, the cutting to form a cut in the elastic material pieces is carried out before application to the first material web. However, it is not necessary for the invention for the cut to be made before application to the liquid-permeable surface layer, but it is also possible within the scope of the invention for the cut to be made after application.

The cutting of the first material web into individual articles may be carried out before application of the elastic pieces.

According to one embodiment, the elastic elements are attached to the first material web in areas outside the absorbent bodies.

According to one embodiment, the cutting into individual articles is carried out along a line which follows the shape of the core.

According to one embodiment, the cut is made so that the distance between the attachment of the elastic element along its longitudinal outer edge and the inner edge formed by the cut is at least 5 mm, preferably at least 10 mm or even better at least 15 mm. According to one embodiment, the cut is made so that the distance between the attachment and the inner edge is at most 40 mm, preferably at most 30 mm or more preferably at most 25 mm.

The attachment of the elastic element is to be interpreted as an area within which the elastic element is attached to the liquid-permeable surface layer. The boundary of this area consists of a line which is drawn through the outermost points at which the elastic element is attached to the liquid-permeable surface layer.

Liquid-permeable surface layer means a liquid-receiving surface which can have liquid-impermeable areas. For example, the area for attaching the elastic element can be liquid-impermeable.

DESCRIPTION OF FIGURES

The embodiments of the invention will be described in greater detail below with reference to illustrative embodiments shown in the accompanying drawings, in which.

DESCRIPTION OF PREFERRED EMBODIMENTS

Figure 1:
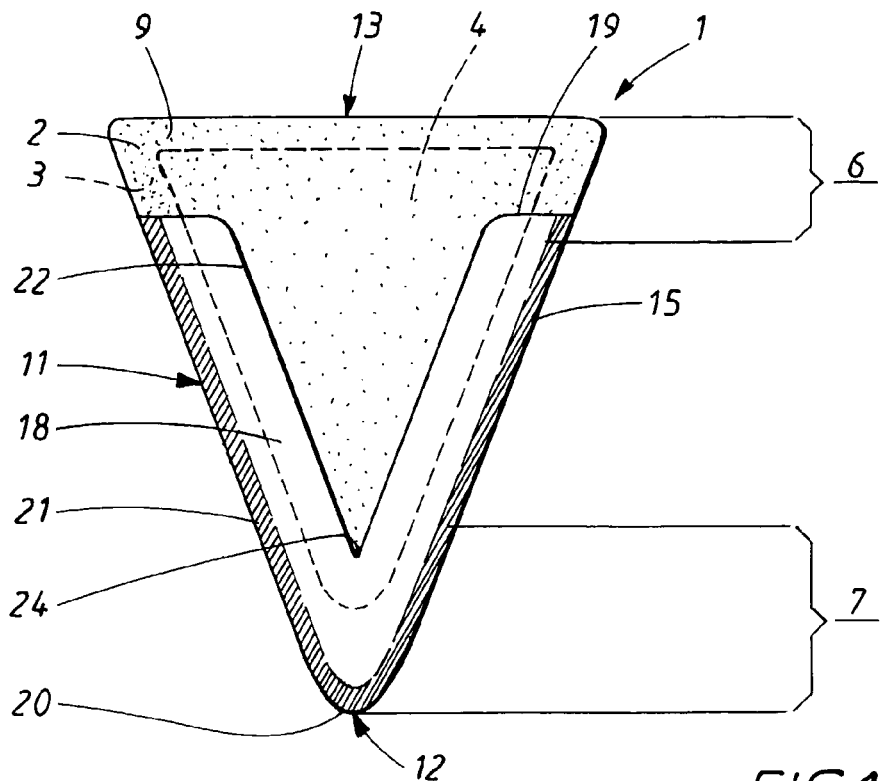
FIG. 1 shows a plan view of an absorbent article according to an embodiment of the invention.
Figure 2:
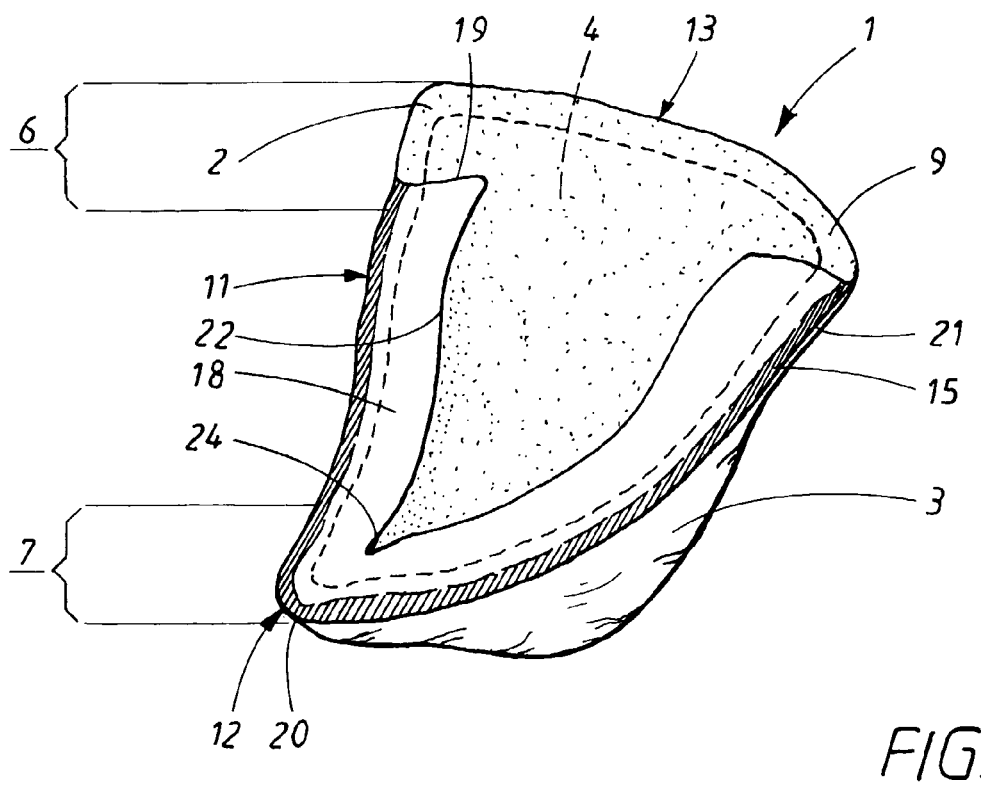
FIG. 2 shows an absorbent article according to an embodiment of the invention in perspective.

The incontinence pad 1 illustrated in FIGS. 1 and 2 comprises an inner liquid-permeable surface layer 2, an outer liquid-impermeable surface layer 3 and an absorbent body 4 arranged between these. The embodiment shown in the figures is essentially triangular. In this connection, the absorbent body 4 tapers from a front end portion 6 towards a rear end portion 7. When the incontinence pad is used, the wider front end portion 6 is intended to be directed forwards in the direction of the abdomen area of the wearer, and the narrower rear end portion 7 is intended to be directed backwards and extend a little way below the penis of the wearer.

The choice of material for the absorbent body 4 is not critical but can be made from among materials or material combinations well known to the expert. For example, the absorbent body 4 can be made from cellulose fluff pulp with superabsorbent material in powder or fibre form mixed in. It is also possible for the greater part of the absorbent body 4 to consist of superabsorbent material.

The outer liquid-impermeable surface layer 3 can, for example, comprise a polymer film comprising, for example, polyethylene or polypropylene, or be of another conventional kind for absorbent articles. The outer liquid-impermeable surface layer 3 can also comprise one or more non-woven layers. A liquid-impermeable film in combination with an outer fibrous layer is suitable if an absorbent article with a more textile-like appearance is desired.

The inner liquid-permeable surface layer 2 can be made from a liquid-permeable non-woven. Another material selection may be perforated films or net.

The outer layer 3 and the inner layer 2 extend with portions 9 outside the absorbent body 4 and are interconnected in these portions 9. Connection can take place by means of, for example, bonding agent, thermobonding or ultrasound bonding.

The incontinence pad in the figures has longitudinal side edges 11, a rear end edge 12 and a front end edge 13.

Arranged over the liquid-permeable surface layer 2 is an elastic element 18. The elastic element 18 is attached to the inner liquid-permeable surface layer 2 in portions 9 arranged laterally outside the absorbent body 4. Attachment has been effected with glue. Instead of glue, use can be made of ultrasonic welding for example. According to the exemplary embodiment shown in FIGS. 1 and 2, the attachment of the elastic element 18 is arranged so as to follow the contour of the absorbent body 4, and it is arranged outside the said contour in the figures. In FIG. 1, the elastic element 18 is attached along its outer edges 21 over its entire length and is also attached to the rear portion along a rear edge 20 of the elastic element 18. The attachment 15 has been made continuous so that no liquid will leak out. The attachment 15 has been effected with glue, but the elastic element 18 can alternatively be attached by welding. A cut 23 has been made in the elastic element 18 in the form of a slit, the edges 22 of which are pulled apart before application of the elastic element 18 to the liquid-permeable surface layer 2. The cut 23 extends through a front edge 19 of the elastic element 18 in the direction of a rear edge 20 to an end point 24 of the cut. By virtue of this, the elastic element 18 has inner edges 22 arranged above the liquid-permeable surface layer 2. In this connection, a pocket has been formed under the elastic element 18, which prevents urine discharged from the wearer from leaking out towards the crotch area. The elastic element 18 is applied over the rear portion 7 of the incontinence pad 1, the incontinence pad 1 having a curved shape in this portion. During use, the rear portion 7 extends a little way in under the scrotum of the wearer.

The elastic element 18 preferably comprises an elastic layer made of an elastic material. Examples of elastic materials include all kinds of natural or synthetic polymeric materials. Examples of elastic polymers which can be used include elastic polyolefins, ethylene-vinyl acetate copolymers (EVA), polyurethane, polyisoprene, butadiene-styrene copolymers, styrene block copolymers such as styrene-isoprene-styrene, styrene-butadiene-styrene or styrene-ethylene/butadiene-styrene block copolymers. Mixtures of only these polymers, or with other modifying elastic or non-elastic materials, can be used within the scope of the invention. The elastic element 18 can comprise layers of different elastic materials and layers of non-elastic materials. The elastic element 18 suitably comprises a non-woven layer arranged against the skin of the wearer. Examples of suitable non-woven materials are spunbond or meltblown which can comprise polyolefin fibres such as polyester, polyethylene, polypropylene and other polyolefin polymers or copolymers. Mixtures of polymers are also possible. The elastic element 18 is preferably hydrophobic, the elastic element 18 constituting a liquid barrier for leakage. It is also conceivable within the scope of the invention for the elastic element 18 to comprise a number of elastic threads which are arranged parallel to one another between outer layers. A cut in such a material is then made between and parallel to two elastic threads.

The cut 23 in the elastic element 18 can be designed in many different ways, as will emerge from the description below. It has been found suitable for the elastic element 18 to have a minimum distance between the attachment 15 and the inner edge 22 of at least 5 mm, preferably at least 10 mm and more preferably at least 15 mm. By virtue of the fact that the elastic element 18 has a distance between the attachment 15 and the inner edge 22 of at least 10 mm, a leakage barrier which prevents leaking out into the crotch and at the sides is obtained. However, the distance between the inner edge 22 and the attachment 15 should not be too great, as it is not desirable for the elastic element 18 to enclose the genitals of the wearer completely. It may then become too warm, by virtue of which the incontinence pad becomes uncomfortable. The distance between the inner edge 22 and the attachment 15 should therefore not be greater than 40 mm, preferably not greater than 30 mm.

In order that the elastic element 18 will function as a liquid barrier against the crotch area of the wearer, it is suitable for the elastic element 18 to be attached to the liquid-permeable surface layer 2 along the rear edge 20 of the elastic element 18 as well. In order that the elastic element 18 will form a barrier against the crotch area, the distance between the end point 24 of the cut in the rear portion and the attachment 15 at the rear edge 20 should be no greater than 50 mm, preferably 40 mm and preferably no greater than 30 mm.

It is also possible within the scope of the invention for the elastic element 18 to consist of a number of separate material pieces joined together with one another. This is not shown in the figures.

The absorbent article can be in the form of an inlay to be fitted in outer pants.

On a side directed outwardly, away from the wearer, of the liquid-impermeable surface layer 3, one or more attachment means for detachable connection to interacting underpants can be provided.

According to FIGS. 1 and 2, the elastic element 18 is intended to be connected over its entire length along its outer longitudinal edges 21 and transverse rear edge 20 and to follow with its connection the contour of the absorbent body 4.

Figure 3:
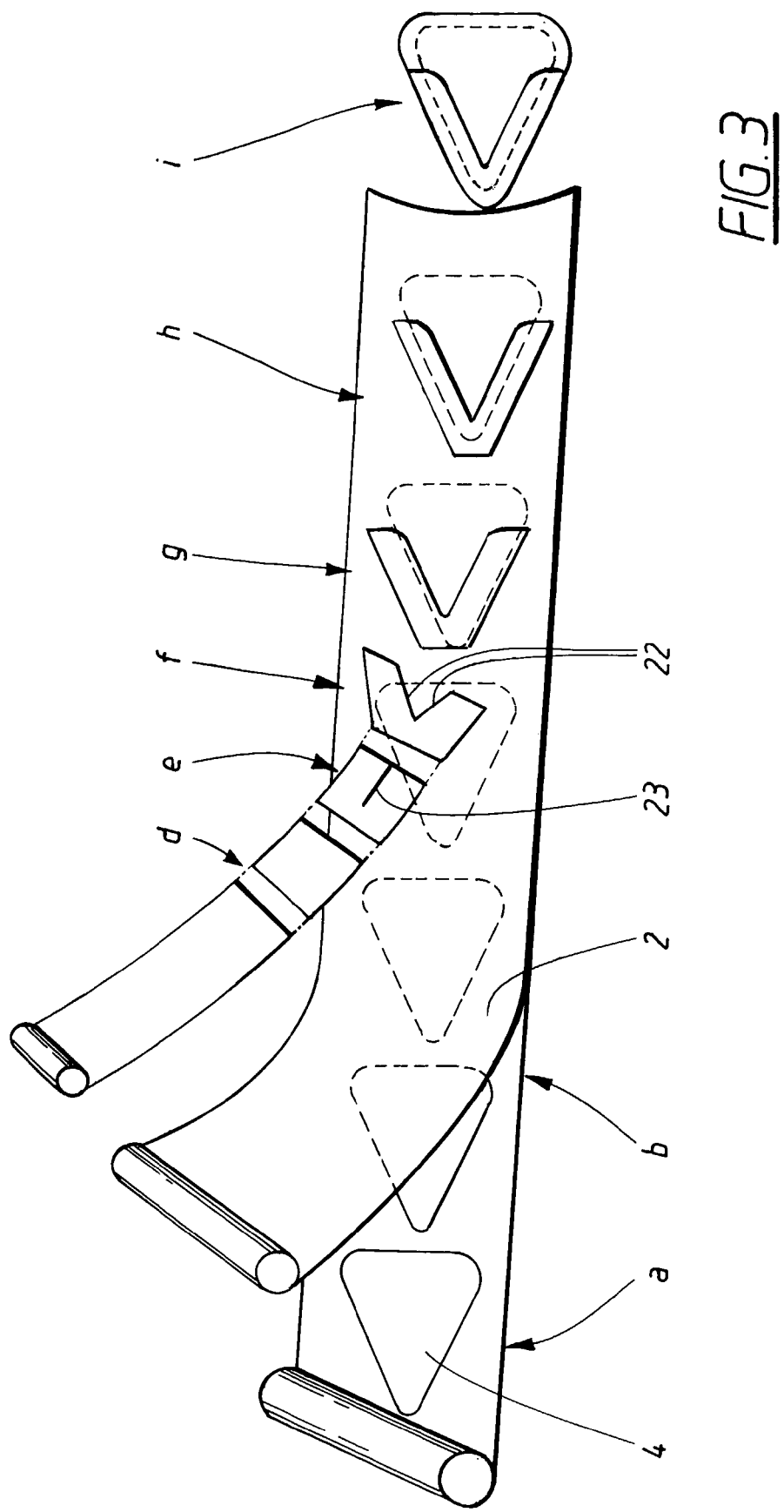
FIG. 3 shows a diagrammatic sketch illustrating the steps for manufacturing an absorbent article according to an embodiment of the invention.

FIG. 3 illustrates the manufacture of absorbent articles 1 according to an embodiment of the invention. At point (a), absorbent bodies 4 are applied with a fixed spacing relative to one another to a first material web running in a transport direction and comprising liquid-impermeable material. The absorbent bodies 4 have a tapering shape from a front end portion 6 towards a rear end portion 7. In the figure, the absorbent bodies 4 have a longitudinal direction in the transport direction of the web. Preshaped absorbent bodies 4 can be applied to the web.

After application of the absorbent bodies 4 to the material web, a liquid-permeable surface layer 2 is applied over the absorbent bodies 4 at (b).

Parallel to the first material web, the elastic pieces 18 to be applied to the liquid-permeable surface layer 2 are cut out. From a continuous web of elastic material which is fed in a transport direction, separate elastic pieces 18 are cut out transversely to the transport direction at (d). In the figure, the material is elastic in its transport direction, but it is also possible for the invention for the material to be elastic transversely to its transport direction. If the material is elastic transversely to its transport direction, it is necessary after cutting to turn the material piece so that the elastic direction of the material coincides with the longitudinal direction of the absorbent articles.

Materials which are elastic in both directions can also be used for the invention.

At point (e), a cut 23 in the form of a slit is made in each elastic piece 18 along an elastic direction of the piece through a front transverse edge 19 in the direction of an opposite rear transverse edge 20 to an end point 24 of the cut. The cut 23 is preferably made centrally between outer longitudinal edges 21 of the material piece. By means of the cut 23, the elastic piece 18 is provided with inner edges 22.

Figure 4:
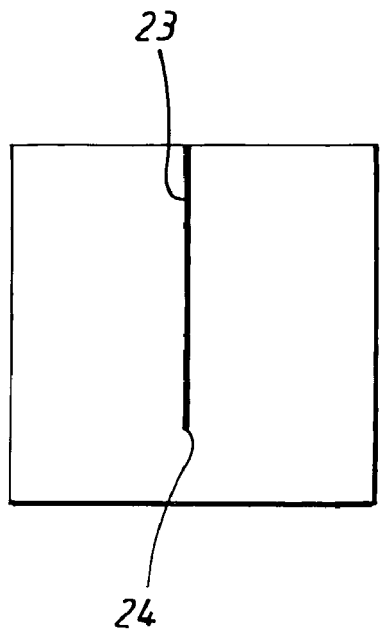
FIGS. 4-7 show plan sketches of elastic pieces according to embodiments of the invention illustrating different cuts.
Figure 5:
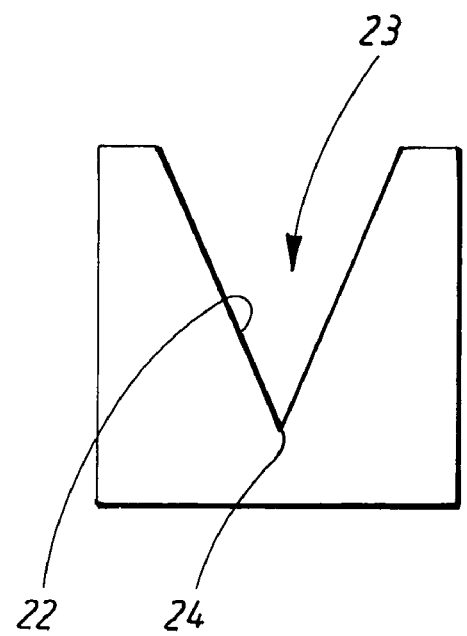
Figure 6:
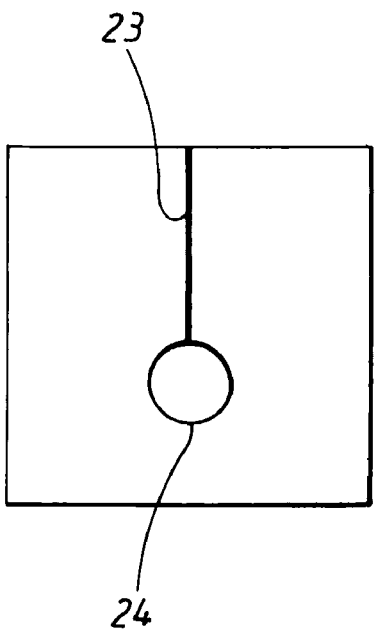
Figure 7:
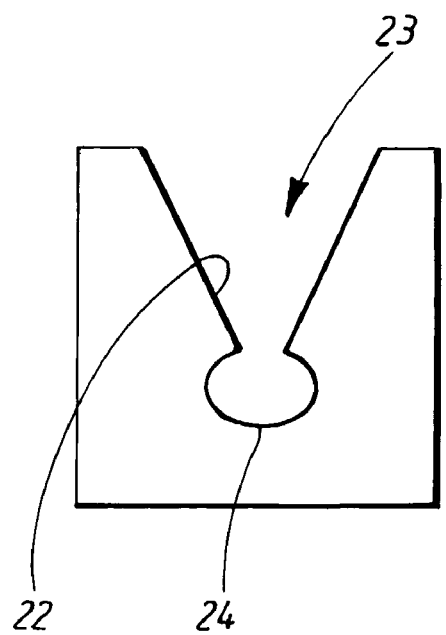

Instead of a slit, a cutout can be made in order to obtain the desired shape of the cut 23. It is not necessary for the cutting to be straight, but it may be desirable to have a curved shape on the inner edges 22 formed after cutting. FIGS. 4-7 show various examples of cuts which can be made in the elastic material piece before application to a product. In FIG. 4, a straight slit has been made. In FIG. 6, a slit has been made and a hole has been cut out at the end of the slit. FIGS. 5 and 7 show different shapes of cutout. The cutout in FIG. 5 has been made so that the cutout follows the shape of the absorbent body 4. In FIG. 7, another hole has been made at the rear end in order better to follow the body shape of the wearer. In the examples shown, the elastic material piece is rectangular before a cutout or a slit is made in the material piece. It is of course alternatively possible to form the elastic element from a material piece of a different shape, for example trapezoidal or triangular.

After the slit has been made, the edges 22 formed by the slit are moved apart, which is illustrated at point (f). If a cutout has been made, it will not be necessary to pull the edges apart as the inner edges 22 are already separated from one another by the cutout. At point (g), the elastic material is stretched in its longitudinal direction in the same direction in which the cut 23 has been made, and it is then attached to the first material web in a stretched state at (h) with glue. Alternatively, the elastic element can be attached using ultrasound or another attachment method.

The elastic material piece is attached to the first material web in areas outside the absorbent body 4. Individual absorbent articles 1 are then cut out from the material web at (i) along a line which follows the shape of the absorbent body 4. When cutting-out takes place, cutting is carried out through the elastic material, the liquid-permeable layer 2 and the liquid-impermeable surface layer 3 in an area outside the absorbent body 4. In this connection, individual absorbent articles 1 are formed which have a portion outside the absorbent body in which an elastic element 18 is attached to the liquid-permeable surface layer 2 in portions outside the absorbent body 4.

The invention is not limited to the illustrative embodiments indicated above, but a number of modifications are possible within the scope of the patent claims which follow.

The invention claimed is:

1. An absorbent article for men comprising:
longitudinal side edges, a rear end edge, a front end edge, an inner liquid-permeable surface layer, an outer liquid-impermeable surface layer, and an absorbent body arranged therebetween,
the absorbent body tapering from a front end portion towards a rear end portion, the absorbent body being arranged so as during use of the article to extend forwards with its wider end portion in the direction of an abdomen area of the wearer and to extend backwards with its narrower end portion a little way below a penis of the wearer, and
a flat web of elastic material attached to the liquid-permeable surface layer at least in the rear end portion of the article and arranged along at least parts of the longitudinal side edges of the article, wherein the flat web of elastic material is attached to the liquid-permeable surface layer along outer longitudinal edges of the flat web of elastic material, and a cut in the form of a slit or cutout is arranged in the longitudinal direction between longitudinal side edges of the flat web of elastic material, which cut extends through a front edge of the flat web of elastic material in the direction of a rear edge to an end point of the cut, the flat web of elastic material being provided by the cut with inner edges arranged over the liquid-permeable surface layer,
wherein the article has a curved shape at least in the rear portion, and a pocket is formed between the flat web of elastic material and the an inner liquid-permeable surface layer, the pocket being open at the front edge of the flat web of elastic material and closed at the rear edge.

2. The absorbent article according to claim 1, wherein the flat web of elastic material is attached to the liquid-permeable surface layer in a pretensioned state.

3. The absorbent article according to claim 1, wherein the flat web of elastic material comprises non-woven material.

4. The absorbent article according to claim 1, wherein the flat web of elastic material is an elastic film.

5. The absorbent article according to claim 1, wherein the flat web of elastic material is joined to the article at an attachment portion of the flat web of elastic material, and a distance between an inner edge obtained by the cut and the adjacent attachment portion of the flat web of elastic material is at least 5 mm.

6. The absorbent article according to claim 1, wherein the flat web of elastic material is joined to the article at an attachment portion of the flat web of elastic material, and a distance between an inner edge obtained by the cut and the adjacent attachment portion of the flat web of elastic material is at most 40 mm.

7. The absorbent article according to claim 1, wherein the flat web of elastic material is attached to the liquid-permeable surface layer along the rear edge of the flat web of elastic material.

8. The absorbent article according to claim 7, wherein the flat web of elastic material is joined to the article at an attachment portion of the flat web of elastic material, and a distance between the attachment portion of the flat web of elastic material along the rear edge and the end point of the cut is less than 50 mm.

9. The absorbent article according to claim 1, wherein the flat web of elastic material is elastic at least in the longitudinal direction of the article.

10. The absorbent article according to claim 9, wherein the flat web of elastic material is also elastic in a transverse direction.

11. The absorbent article according to claim 1, wherein the absorbent article is an insert which is intended to be used in combination with outer pants.

12. The absorbent article according to claim 1, wherein the article is provided with one or more attachment means arranged on a side directed outwardly, away from the wearer, of the liquid-impermeable surface layer, which attachment means are intended to hold the absorbent article in the intended place inside underpants.

13. The absorbent article according to claim 5, wherein the flat web of elastic material is joined to the article at an attachment portion of the flat web of elastic material, and a distance between an inner edge obtained by the cut and the adjacent attachment portion of the flat web of elastic material is at most 40 mm.

14. The absorbent article according to claim 1, wherein the flat web of elastic material is a layer consisting of elastic non-woven or a laminate of non-woven and an elastic plastic film.

15. The absorbent article according to claim 1, wherein the flat web of elastic material further comprises a non-elastic layer.

16. The absorbent article according to claim 1, wherein the flat web of elastic material is a layer extending along both longitudinal and transverse directions of the elastic element from edge to edge thereof.

* * * * *